United States Patent [19]
Lee et al.

[11] Patent Number: 6,082,174
[45] Date of Patent: Jul. 4, 2000

[54] APPARATUS AND METHOD FOR DETERMINING THE AMOUNT OF ENTRAPPED GAS IN A MATERIAL

[75] Inventors: Charles E. Lee, Union City; John D. Della-Santina, Novato, both of Calif.

[73] Assignee: Benchtop Machine and Instrument, Inc., Fairfax, Calif.

[21] Appl. No.: 09/132,630

[22] Filed: Aug. 11, 1998

[51] Int. Cl.$^7$ ............................ G01N 33/38; G01N 37/00
[52] U.S. Cl. ........................................... 73/19.08; 73/60.11
[58] Field of Search ................................. 73/60.11, 19.08, 73/19.05, 19.01, 19.09, 19.1

[56] References Cited

U.S. PATENT DOCUMENTS

| | | | |
|---|---|---|---|
| 2,138,141 | 11/1938 | Cromer et al. | 73/19.05 |
| 2,280,086 | 4/1942 | Hayward | 324/693 |
| 2,749,220 | 6/1956 | Rochon | 436/32 |
| 3,521,478 | 7/1970 | Magorien | 73/19.05 |
| 3,731,530 | 5/1973 | Tanguy et al. | 73/152.42 |
| 3,766,786 | 10/1973 | Gebatia et al. . | |
| 4,072,046 | 2/1978 | Lao . | |
| 4,083,228 | 4/1978 | Turner et al. . | |
| 4,095,473 | 6/1978 | Batchelor et al. . | |
| 4,184,371 | 1/1980 | Brachet . | |
| 4,329,869 | 5/1982 | Toda | 73/19.08 |
| 4,369,652 | 1/1983 | Gundlach . | |
| 4,416,154 | 11/1983 | Schaffer et al. . | |
| 4,573,342 | 3/1986 | Jones . | |
| 4,640,130 | 2/1987 | Sheng et al. . | |
| 4,700,561 | 10/1987 | Dougherty | 73/19.05 |
| 4,837,776 | 6/1989 | Poll | 374/56 |
| 4,852,395 | 8/1989 | Kolpak | 73/61.44 |
| 4,969,356 | 11/1990 | Hartstein . | |
| 5,022,261 | 6/1991 | Wolfson et al. . | |
| 5,074,146 | 12/1991 | Orr et al. . | |
| 5,133,219 | 7/1992 | Camp . | |
| 5,535,624 | 7/1996 | Lehmann . | |
| 5,576,499 | 11/1996 | Davies . | |

OTHER PUBLICATIONS

Product brochure for Volumetair; Press–Ur–Meter; and Roll–A–Meter, A Simple Device for Measuring Entrained Air, Gilson Company, Inc., 8 pages, Aug. 1997.

Standard Test Method for Air Content of Freshly Mixed Concrete by the Pressure Method, ASTM Designation C231–91b, pp. 130–137, Jan. 1992.

Standard Test Method for Open–Cell Content of Rigid Cellular Plastics by the Air Pycnometer, ASTM Designation D 2856–94, pp. 143–147.

*Primary Examiner*—Hezron Williams
*Assistant Examiner*—Jay L. Politzer
*Attorney, Agent, or Firm*—James C. Peacock III; John P. O'Banion

[57] ABSTRACT

An entrapped gas measuring apparatus includes a reservoir housing with a reservoir which is adapted to receive a material sample and to expand according to an expansion of the material sample when a negative pressure is applied externally to the reservoir. A parameter indicating the change in volume of the reservoir during the expansion, such as the actual change of volume of the reservoir or a change in position of a moveable wall which at least in part defines the reservoir, is detected by a detector. A processor coupled to the detector is used to determine the amount of entrapped gas based upon the detected parameter. The amount of entrapped gas determined by the processor may be the percent volume of the entrapped gas in relation to the overall volume of the sample, or may be the actual volume of the entrapped gas in the sample. Based at least in-part upon the measured amount of entrapped gas within the sample, the processor is further adapted to determine at least one of: percent volume of the substrate in the sample in relation to the overall volume of the sample; actual volume of the substrate in the sample; or density of the sample or substrate within the sample. The entrapped gas measuring apparatus may be used to produce a material having a known amount of entrapped gas by: making a first material according to a first method and which has a first amount of entrapped gas; applying a negative pressure to the sample such that the sample expands from a first volume to a second volume; detecting a parameter which is indicative of the change of sample volume under the applied negative pressure; comparing the detected parameter with a predetermined range for the parameter; and, if the detected parameter is not within the predetermined range, making a second material according to a second method which has a second amount of entrapped gas that is within the predetermined range.

16 Claims, 7 Drawing Sheets

Typical Sample Syringe Sizes

| Syringe size (ml) | 1 | 5 | 10 | 30 | 60 |
|---|---|---|---|---|---|
| $d_O$ (mm) | 98.6 | 89.5 | 107.6 | 135.9 | 163.0 |
| C (mm/ml) | 59 | 9.0 (45/5ml) | 6.1 (61.1/10ml) | 3.28 (98.3/30ml) | 1.80 (108/60ml) |
| ld (mm) | 4.56 | 11.9 | 14.3 | 20.8 | 26.28 |
| Max. $d_2$ (mm) | 157.6 | 134.5 | 168.7 | 234.2 | 271.0 |

APPARATUS AND METHOD FOR DETERMINING THE AMOUNT OF ENTRAPPED GAS IN A MATERIAL

FIELD OF THE INVENTION

The present invention is a test instrument and method. More specifically, it is a device assembly and test method for determining the amount of entrapped gas within a material sample, including a method of manufacturing a material with a predetermined amount of entrapped gas based upon use of the device assembly and test method.

BACKGROUND OF THE INVENTION

In many industries, there is a need to control the volume of entrapped gas in a variety of materials so that more desirable products may be achieved. The terms "entrapped gas" are herein intended to mean the volume of gas which is entrapped or entrained within a substrate in a material or sample. Furthermore, the terms "material" or "sample" are herein intended to consist of: (1) a substrate, such as a liquid, solid, or semi-solid; and (2) entrapped gas which is a gas that is in a gaseous state and not dissolved within the substrate. Therefore, in simplified terms, entrapped gas means "bubbles" of gas which are trapped within the substrate of a material sample, which bubbles may have a volume or size ranging from visible to microscopic or sub-microscopic.

Examples of known uses for measuring entrapped gas in products are many. For example, in an industrial setting it is believed that the durability of concrete may be increased by controlling the amount of entrapped gas to a predetermined level within a concrete substrate prior to setting. In another example, various consumer goods are also believed to rely in part upon controlling the amount of entrapped gas in order to be sold and used in a reliable and consistent condition. Such consumer goods may include, without limitation: creams and ointments, such as for use in beauty care; pastes, such as toothpaste; or various food substances, such as for example whipped cream. In still a further example, various medical products also require the ability to control the volume of entrapped gas within a particular substrate in order to achieve a reliable, safe product which provides an intended result during use. Further more specific examples of such medical products include, without limitation: pharmaceuticals; and medical creams, gels, and ointments.

Furthermore, the ability to control the gas content in a material is closely related to, and in fact largely dependent upon, the ability to measure the entrapped gas volume in the overall material. Therefore, the ability to measure the entrapped gas volume may be of paramount importance in the quality control of producing such materials.

In one respect, measurement of entrapped gas volume may provide indicia of certain qualities of the overall material sample. For example, the porosity of a sample is a direct consequence of the entrapped gas volume within the sample and the determination of porosity of certain materials is often desirable. In another example, for materials such as cement, sand, gravel, and other admixtures and aggregates, it is believed that the specific gravity and moisture content of the overall sample can be assessed at least in part based upon the known volume of entrapped gas.

In another respect, measurement of entrapped gas volume may also provide for the determination of specific properties of the substrate within the sample, such as substrate volume and density. It is believed that accurate determination of the density and volume of a substrate in a material sample may facilitate the production for certain types of materials. For example, density determinations can be used as a diagnostic tool for identifying purity of the substances which form the substrate or for indicating adulterations in preparation of known compositions. Further to this need, measurement of entrapped gas volume may provide for a direct determination of substrate volume, and therefore substrate density. Substrate volume may be calculated by subtracting entrapped gas volume from the overall sample volume. Thereafter, substrate density may determined by multiplying the substrate volume by the substrate mass.

Conventional Devices and Methods for Measuring Entrapped Gas Volume

Various devices and methods have been previously disclosed for measuring entrapped gas volume. For example, one known method for entrapped gas volume includes exposing a sample to acoustic or subsonic waves. However, it is believed that such known methods do not accurately and reliably reflect the true amount of entrapped gas. Further more specific examples of devices and methods of this type are variously disclosed in the following references: U.S. Pat. No. 4,184,371; and U.S. Pat. No. 4,640,130. The disclosures of these documents are herein incorporated in their entirety by reference thereto.

Another type of previously disclosed device which is intended to indirectly measure substrate volume in a sample by measuring entrapped gas volume is known as the "gas pycnometer." In general, known gas pycnometers operate by applying a positive pressure either to a chamber which contains the sample or to a chamber which connects to a first chamber which contains the sample. A gas having a small molecular size, such as helium, may be used for providing the positive pressure by entery into the pores of the sample thereby displacing the gas, e.g. air, previously absorbed in the pores of the sample. Consistent with the gas law stated below, the sample volume can be determined by measuring pressure change while volumes are kept constant or by changing the volumes and maintaining pressure within the device. For example, two chambers may be used and one chamber injected with gas. The pressure is measured and the gas allowed equalize between the sample chamber and the adjoining chamber. The pressure in the combined volume is measured and related to the sample volume. The gas law relied upon is the following:

$PV=nRT$, wherein

P=pressure

V=volume n=number of moles of gas

R=gas constant

T=absolute temperature.

Further more specific examples of gas pycnometry devices and methods such as those just provided above are variously disclosed throughout the following references: U.S. Pat. No. 5,133,219; U.S. Pat. No. 5,074,146; U.S. Pat. No. 4,095,473; and U.S. Pat. No. 4,083,228. The disclosures of these documents are herein incorporated in their entirety by reference thereto.

SUMMARY OF THE INVENTION

The present invention is an assembly and method for measuring an amount of entrapped gas in a material sample based upon the expansion of the entrapped gas when the sample is exposed to a vacuum.

In one mode of the invention, an entrapped gas measurement apparatus includes a housing with a wall which defines at least a portion of a reservoir which is adapted to receive the material sample. The wall has an adjustable position from a first position to a second position such that the reservoir has an adjustable volume from a first volume to a second volume, respectively, when the material sample is received within the reservoir and when a predetermined force is applied to the wall outwardly of the reservoir. The position of the wall is indicative of the volume of the reservoir. A detector is coupled to the housing and is adapted to measure the position of the wall. A processor is coupled to the detector and is adapted to determine an amount of entrapped gas within the material sample based upon a change in the position of the wall from the first position to the second position. According to this assembly, the first volume of the reservoir is substantially equal to a volume of the material sample at an initial equilibrium force condition and prior to applying the predetermined force to the wall. Furthermore, the second volume of the reservoir is substantially equal to the volume of the material sample under a vacuum force condition after applying the predetermined force to the wall with a force applicator.

In a further aspect of this mode, the housing and reservoir are of a syringe-type configuration. The reservoir is further defined by a reservoir chamber which is relatively rigid, and the wall is moveable relative to and encloses the reservoir chamber. The wall according to this aspect has a zero position relative to the reservoir chamber which is characterized by the reservoir's volume being substantially equal to zero prior to receiving the material sample within the reservoir. When the first position of the wall and initial equilibrium force condition are further characterized by an equilibrium force on the wall at atmospheric pressure, the processor determines the amount of entrapped gas at atmospheric pressure by the equation: $(d_2-d_1)/(d_1-d_0)* 100[P_a/(P_a-P_v)-1]$, such that $d_o$ is the zero position, $d_1$ is the first position, $d_2$ is the second position, $P_a$ is atmospheric pressure, and $P_V$ is a pressure which equals the predetermined force.

In still a more detailed variation of this syringe-type aspect, the housing includes a barrel and a plunger. The barrel has an inner surface which forms an inner bore with a longitudinal axis that extends between a front end and a rearward end. The plunger has a front end and a rearward end. A front wall is removably engaged to and is adapted to form a gas tight seal with the front end of the barrel. The front end of the plunger is engaged within the barrel's inner bore through the rearward end of the barrel, and the wall is secured to the front end of the plunger and rearward wall slideably coupled to the barrel's inner surface with a gas tight seal. According to this configuration, the reservoir is therefore defined by the front wall, the barrel's inner bore, and the rearward wall. The first and second positions of the wall according to this variation are along the longitudinal axis of the barrel's inner bore.

In another aspect of this apparatus mode, the processor may be adapted to determine one of several parameters related to the amount of entrapped gas in the sample. In one variation, the processor is adapted to determine the amount of entrapped gas as a percent volume of the sample which represents an actual volume of entrapped gas within the material sample divided by the volume of the material sample. In another variation of this aspect, the processor is adapted to determine the actual volume of entrapped gas within the material sample which represents the percent volume of entrapped gas multiplied by the volume of the material sample. In a another variation, the processor is adapted to determine a volume of the substrate within the sample based upon either the percent volume of the entrapped gas or the actual volume of entrapped gas within the sample. In yet another variation, the processor is adapted to determine a density of the substrate based in-part upon the volume of the substrate.

In a further aspect to the entrapped gas measurement assembly mode, a force applicator may be included in the assembly such that it is adapted to couple to the wall and is adapted to apply a predetermined force to the wall outwardly of the reservoir.

In one variation of this aspect, the force applicator includes a vacuum source which is coupled to the wall and which is adapted to apply a negative pressure to the wall. According to a further variation, a vacuum chamber houses at least a portion of the housing that includes the wall, and the vacuum source is coupled to the vacuum chamber and is adapted to apply a negative pressure within the vacuum chamber. In the alternative to the vacuum source variation, the force applicator may also be mechanically coupled to the wall and adapted to mechanically apply the predetermined force to the wall.

Another mode of the present invention is a method for measuring an amount of entrapped gas in a material sample. According to this method, the material sample is added to a reservoir which is defined at least in part by a wall and which has a volume that is substantially equal to the sample volume. After adding the material sample to the reservoir, a force is applied upon the wall outwardly of the reservoir such that the reservoir and material sample expand from a first volume to a second volume. A parameter which is indicative of a change in reservoir volume after applying the force upon the wall is detected and measured, which detected and measured parameter is used to determine an amount of entrapped gas within the material sample. The detected parameter according to this method is at least one of the reservoir volume or a second position of the wall relative to first position of the wall prior to applying the force to the wall, which second position of the wall is characterized by the change in reservoir volume.

In one aspect of this method mode of the invention, the reservoir is defined at least in part by a barrel and a plunger, the plunger having a plunging end which is slideably engaged within the barrel to form the wall. The method according to this aspect further includes detecting a position of the plunging end after applying the force to the wall. The amount of entrapped gas within the material sample is then determined based upon the detected position of the plunging end relative to an initial position of the plunging end prior to applying the force onto the wall and also relative to a zero position of the plunging end prior to adding the material sample to the reservoir.

In a further variation of the syringe-based aspect of this method mode, a vacuum source is coupled to the wall. Thereafter, a vacuum pressure is applied to the wall with the vacuum source outwardly from the reservoir.

A further method mode for measuring an amount of entrapped gas within a material sample according to the present invention includes: applying negative pressure to the material sample, wherein the material sample changes from a first volume to a second volume, and detecting a change in volume from the first volume to the second volume determining an amount of entrapped gas in the sample based on the change in volume, wherein the amount of trapped gas is one of either a percent volume of the entrapped gas within the material sample relative to an overall volume of the material sample or an actual volume of entrapped gas within the material sample.

Still a further method mode for producing a material with a predetermined amount of entrapped gas according to the present invention includes: forming a first material according to a first method with a first amount of entrapped gas; applying negative pressure to a sample of the first material, wherein the sample changes from a first volume to a second volume; detecting the change in volume; determining the amount of entrapped gas in the sample based on the change in volume; comparing the determined amount of entrapped gas with a predetermined range of values; and, when the determined amount of entrapped gas differs from the predetermined range of values, forming a second material according to a second method with a second amount of entrapped gas.

Thus, it is an object of the present invention to provide an assembly which can directly and accurately determine the amount of entrapped gas in a variety of samples.

It is a further object of the present invention to provide an apparatus which can easily and accurately determine the density of a variety of samples.

It is another object of the present invention to provide an gas measurement apparatus which is easy to use and require little expertise by the operator.

Other objects and advantages of the present invention will become more readily apparent from the following description of preferred embodiments.

DETAILED DESCRIPTION OF THE INVENTION

The present invention is an assembly which is adapted to measure entrapped or entrained gas volume within a material sample by applying negative pressure to the sample, measuring the resulting expansion of the sample in response to the negative pressure, and thereafter calculating the amount of gas in the sample. The terms "amount of gas" or variations thereof are herein intended to mean percent (%) volume of the overall sample volume or the actual volume of the entrapped gas within the material sample.

In general, the entrapped gas measurement apparatus of the present invention uses a reservoir housing assembly with a reservoir which houses a material sample to be measured. A detector monitors the reservoir's expansion under an applied negative pressure, which expansion is a direct concomitant to the sample's expansion under a vacuum formed within the reservoir. A processor is adapted to determine the amount of entrapped gas within the sample based upon the expansion of the reservoir and sample.

FIGS. 1A–D show one reservoir housing assembly (1) according to sequential modes of use in an entrapped gas measurement assembly according to the present invention. As shown variously throughout these FIGS. 1A–D, reservoir housing assembly (1) is a syringe-type device which includes a barrel (10), a plunger (20), and a loading assembly (30).

Figure 1A:
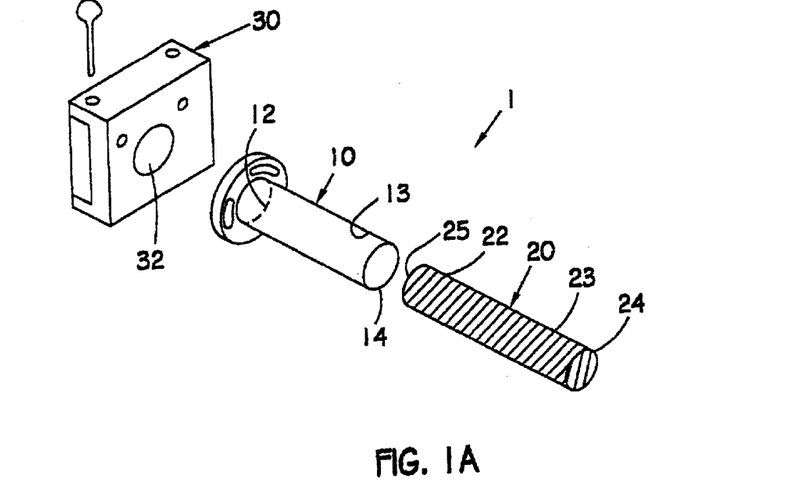
FIGS. 1A thought 1D show schematic perspective views of a reservoir housing assembly for one entrapped gas measurement apparatus during sequential modes of use according to the present invention.

In more detail to the components shown in FIGS. 1A, barrel (10) includes an inner surface (13) which defines an inner bore that extends between a front end (12) and a rearward end (14). Plunger (20) includes a shaft (23) which extends between a plunging end (22) and a detection end (24). Plunging end (22) of plunger (20) includes a rearward wall (25) which is adapted to slideably engage inner surface (13) of barrel (10) with a gas tight seal when rearward wall (25) and plunging end (22) are introduced through reaward end (14) and into the inner bore of barrel (10). Loading assembly (30) includes a front wall (32) which is adapted to removably engage barrel (10) such that a material sample to be measured may be loaded within barrel (10) and then enclosed therein with a substantially gas tight seal.

A combination assembly of the various components for reservoir housing assembly (1) just shown and described by reference to FIG. 1A is further shown in FIGS. 1B–D, wherein a reservoir is provided and defined by the combination of front wall (32), inner surface (13) of barrel (10), and rearward wall (25) of plunger (20).

Figure 1B:
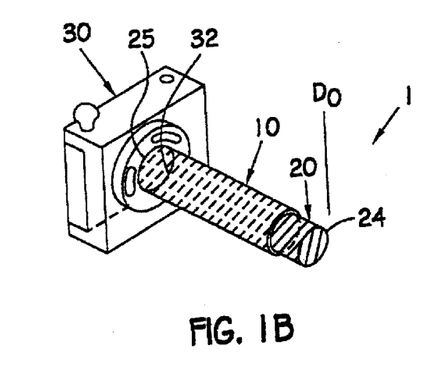

The first sequential mode of use for reservoir housing assembly (1) is shown in FIG. 1B, wherein rearward wall (25) is advanced within the inner bore of barrel (10) such that it contacts or is positioned closely adjacent to the front wall (32) of loading assembly (30). In this configuration, the volume of the reservoir is substantially zero and a baseline or "zero" position $D_0$ for rearward wall (25) of plunger (20) is designated by the position of the plunger's detection end (24) which extends outside the barrel. This zero position $D_0$ is used as a starting reference point for measuring a change in volume of the reservoir during subsequent modes of use according to FIGS. 1C–D as a material sample to be measured is loaded into the reservoir and then acted upon to expand in the reservoir under an applied negative pressure force.

Figure 1C:
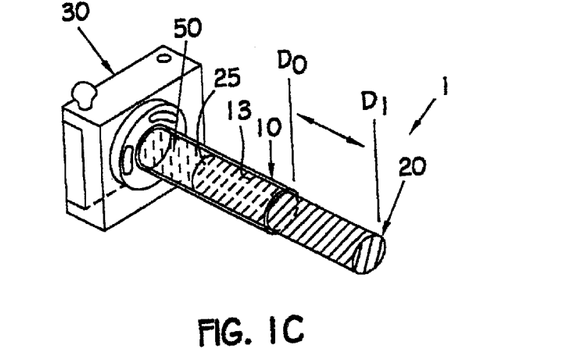

FIG. 1C shows reservoir housing assembly (1) after a material sample (50) is added to barrel (10) through loading assembly (30) and both front wall (32) and rearward wall (25) are made to contact and completely confine sample (50). Thus, the reservoir formed by front wall (32), inner surface (13), and rearward wall (25) has a volume which is substantially equal to the volume of the material sample to be measured. Further to this "sample loading" mode of use, the new position of the plunger's detection end (24) designates a first position $D_1$ for rearward wall (25), and therefore a first volume $V_0$ when the sample is under ambient atmospheric pressure. Thus, the movement of rearward wall (25) of plunger (20) from the first position $D_0$ to the second position $D_1$ indicates a baseline wall movement which is representative of first volume $V_1$ for the reservoir.

Figure 1D:
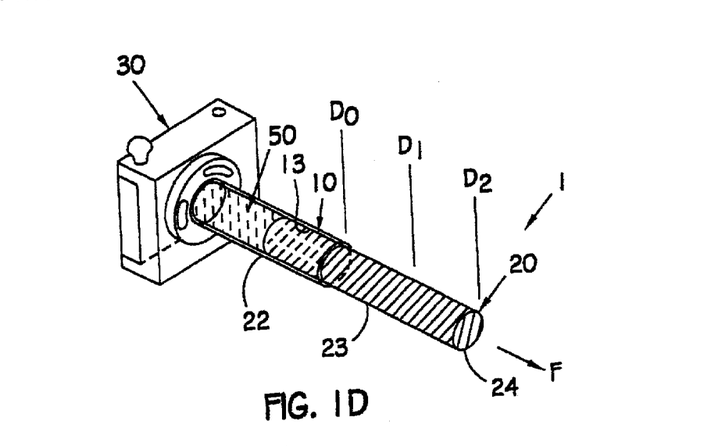

The next sequential mode of use for reservoir housing assembly (1) is shown in FIG. 1D, wherein the portion of plunger (20) which extends outwardly from barrel (10) is exposed to a predetermined force F which forms a negative pressure that in turn places a force on the plunger (20) outwardly of the reservoir. This pressure is translated to rearward wall (25) by virtue of the rigid coupling via shaft (13) of the plunger (20), and is further translated from rearward wall (25) and to sample (50) contained within the reservoir. Sample (50) responds to the negative pressure by expanding by a differential volume which is proportional to the amount of gas entrapped within the sample. The amount or volume which a given sample expands is determined by the expansion reaching a final equilibrium, which may be asymptotic or absolute, which equilibrium is believed to be defined by the pressure of the entrapped gas (which changes during expansion) approaching the negative pressure applied to the sample. Moreover, the force against the rearward wall (25) during sample expansion adjusts that wall outwardly along the length of the inner surface (13) of barrel (10), at least until rearward wall (25) reaches an equilibrium position which is identified by a second position $D_2$ for detection end (24) of the plunger (20). Thus, the plunger's movement along the distance between first position $D_1$ and second position $D_2$ indicates and is proportional to the change in the volume of the reservoir, and thus of the sample, between the first volume $V_1$ and a second volume $V_2$.

As summarized initially above and will be further described in more detail below, the changing position of the plunger is directly proportional to the volumetric change of the reservoir during the expansion of the sample under negative pressure, and the volumetric change of the sample and reservoir is directly proportional to the amount of entrapped gas within the sample. Therefore, the entrapped gas measurement apparatus of the present invention identifies the volumetric change of the reservoir by measuring the positioning reference points ($D_1$ an $D_2$) of the moveable rearward wall by use of a detector (not shown). Based upon the detector's measurement, a processor (also not shown), such as a computer, determines the amount of gas entrapped in the sample.

According to one operable mode for a processor which is believed to be highly beneficial for use with the specific syringe-type embodiment just shown and described by reference to FIGS. 1A–D, the amount of entrapped gas within a material sample is determined as a percent (%) volume of entrapped gas. One particularly beneficial mode for making this percent volume determination is based upon the detected plunger position according to the following relationships, or variations thereof:

(1) $[((V_E \times P_V)/V_S)/1-P_2] \times 100 = \%$ air at atmospheric pressure; and (2) $[(D_2-D_1)/[(D_1-D_0)*(Pa/P_2)-1]] \times 100 = \%$ air at atmospheric pressure; and therefore, (3) $(D_2-D_1)/(D_1-D_0)*100/[P_A/P_A-P_v)-1] = \%$ air at atmospheric pressure;

wherein

C=Volume constant of the reservoir;
$V_s = C(D_{1-D0})$=Sample Volume at Atmospheric Pressure;
$V_2 = C(D_2-D_0)$=Sample Volume after Expansion;
$V_E = V_2 - V_S$=Expansion Volume under Applied Vacuum ($P_v$);
$V_E = CD_2 - CD_1$;
$D_0$=Distance between detection end and front wall (without sample);
$D_1$=Distance between detection end and front wall (with sample);
$D_2$=Distance between detection end and front wall (before vacuum);
$P_A$=Atmospheric pressure;
$P_v$=Vacuum pressure; and
$P_2 = P_A - P_V$.

Moreover, according to the relationship between plunger position and applied pressure just described by equation "(3)" above, an additional altitude correction factor may also be considered in determining the amount of entrapped gas with the processor, wherein atmospheric pressure $P_A$ is usually within the range of 0.75 atm to 1.10 atm. It is further contemplated therefore that "vacuum pressure" may be any pressure which is negative relative to a baseline which is the atmospheric pressure in the test environment.

Further to the syringe-type barrel-and-plunger embodiment of FIGS. 1A–D, the volume constant C provided in the analysis above for arriving at the relationship shown by equation "(3)" represents the volume per unit length of the barrel. In a cylindrical, non-tapered barrel, this parameter is a direct construct of the cross-sectional area of the barrel and a constant for the purpose of determining volume of the reservoir over ranges of distances along the barrel (the only variable for reservoir volume is the moveable, rearward wall). It follows that, for syringe barrels which are not cylinders of constant diameter or cross-sectional area, the constant C may be required as a variable in the final determining equation.

Figure 2:
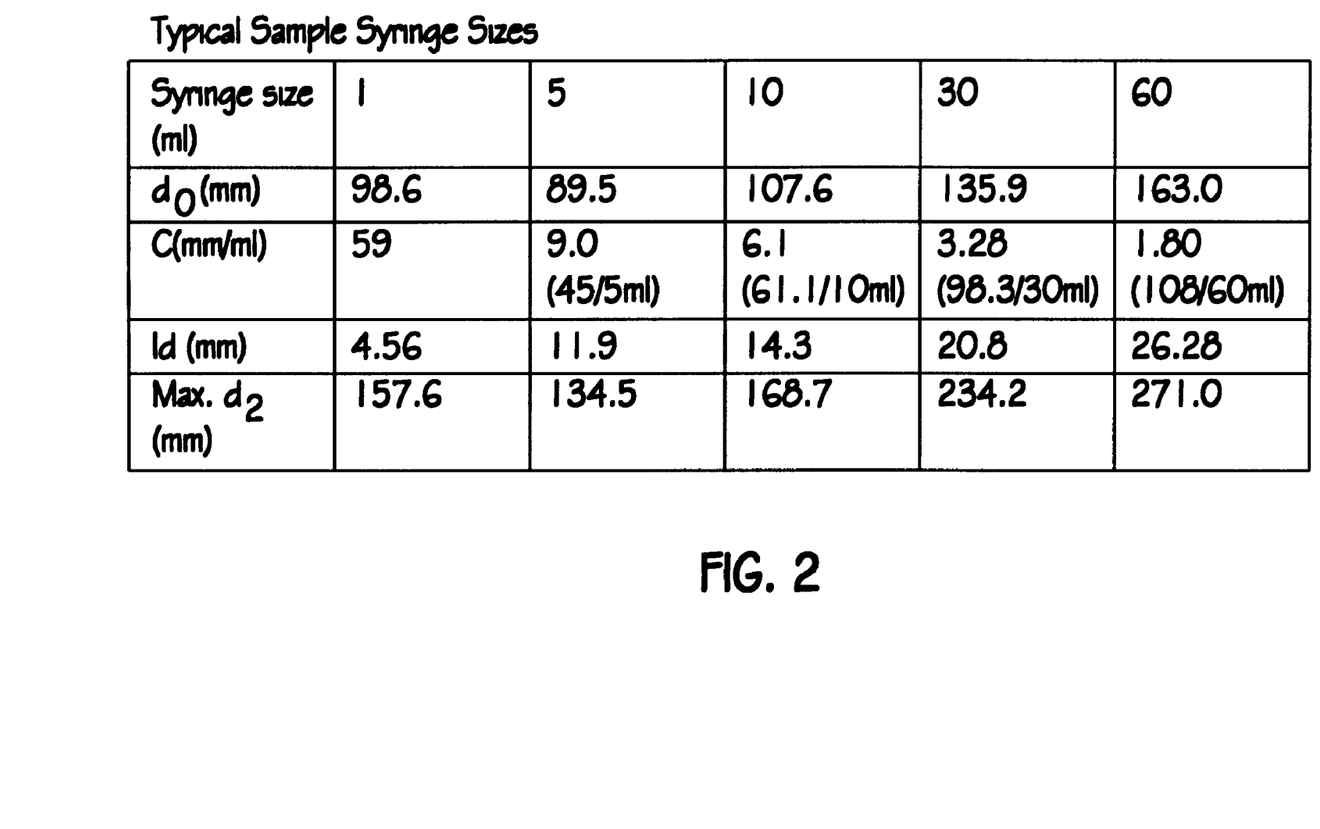
FIG. 2 shows a table of exemplary syringe sizes for use in a reservoir housing assembly such as that shown schematically in FIG. 1.

Still further to the syringe-type barrel-and-plunger embodiment just shown and described by reference to FIGS. 1A–D, FIG. 2 additionally illustrates measurements taken for typical reference points and other salient characteristics of varying syringe sizes which are believed to be particularly adapted for use according to the present invention with samples having volumes ranging from 0 to 10 ml. The syringes represented by the FIG. 2 table have volumes which range from 1 to 60 milliliters. Also represented in the table of FIG. 2 are the following syringe parameters: the zero position of the detection end for the plunger which is indicated by a distance from the front wall of the reservoir, or "$D_0$" (essentially representing the length of the plunger shaft); the syringe volume constant which is indicated by "C" (or the cross-sectional diameter of the barrel of the syringe); the inner diameter of the syringe which is indicated in the table as "id"; and the maximum distance that the opposite wall of the plunger can move to a second position after applying a vacuum pressure to the sample, which distance is indicated by the distance from the detecting end of the plunger to the front wall, or "$D_2$".

Figure 3:
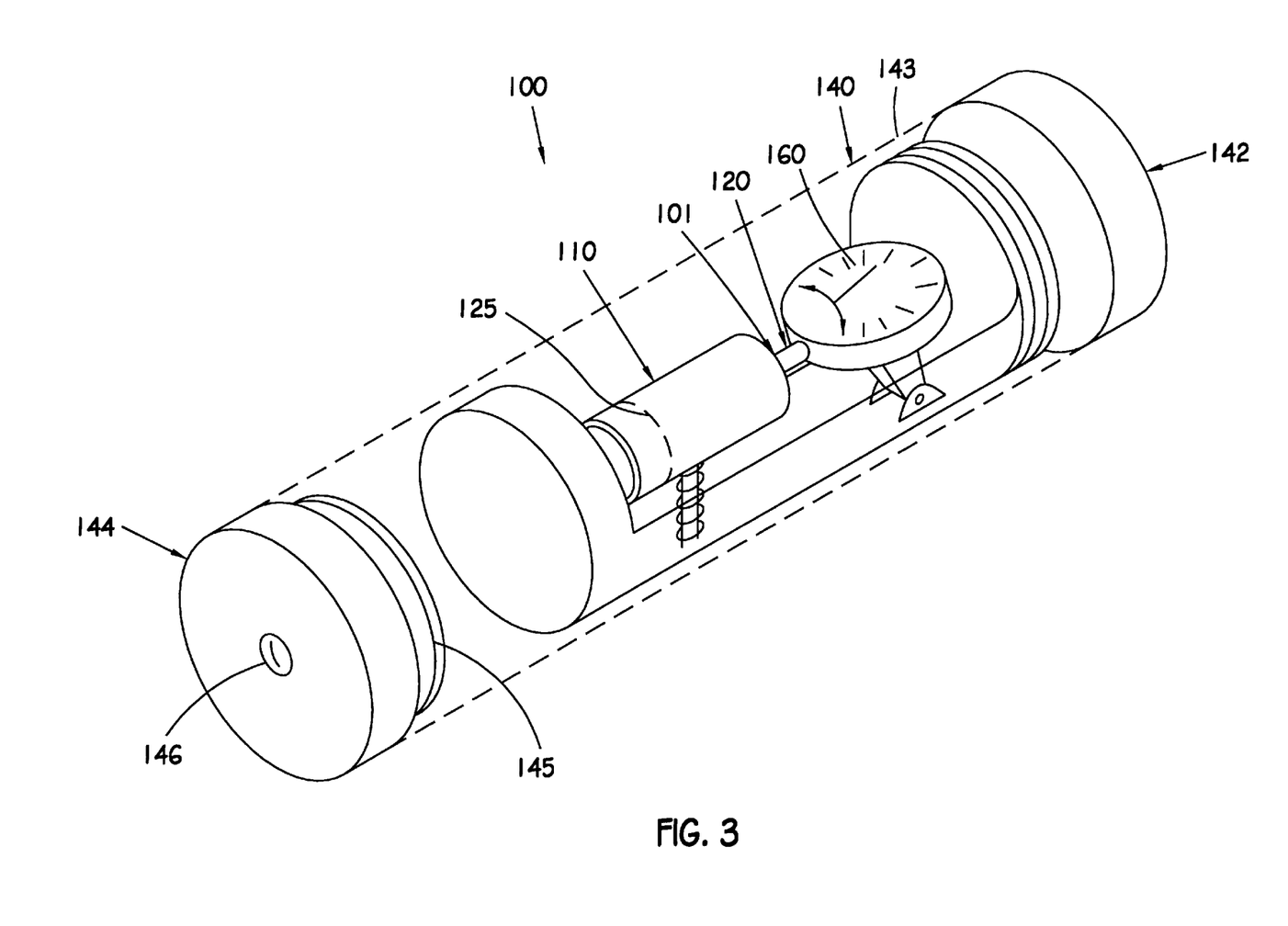
FIG. 3 shows a perspective view of one entrapped gas measurement apparatus for measuring entrapped gas in a material sample according to the sequential modes of use shown schematically in FIG. 1.

FIG. 3 shows one more detailed embodiment of an entrapped gas measurement apparatus (100) which utilizes a reservoir housing assembly such as that just shown and described by reference to FIGS. 1A–D above. Entrapped gas measurement apparatus (100) includes a vacuum chamber (140) having a transparent cover (143) which is adapted to couple to a negative pressure source (not shown). The chamber contains a reservoir housing assembly (101) that forms a reservoir which is adapted to receive and hold the sample and is similar to the reservoir housing assembly shown in FIGS. 1A–D.

Movement of the plunger's rearward wall (125) is determined by measuring the position of detection end (not shown) of plunger (120) with detector (160), which is coupled to the plunger (120). In the particular variation shown in FIG. 3, detector (160) is a linear measuring element and is attached to the plunger at the detecting end of the plunger. The present invention contemplates that the detector may be adapted to detect the change in plunger position according to a variety of suitable known mechanisms, including but not limited to optical, electrical, or mechanical mechanisms known in the art. In addition, other various measuring parameters may also be suitable, such as the measurement of pressure changes in the reservoir.

Figure 6:
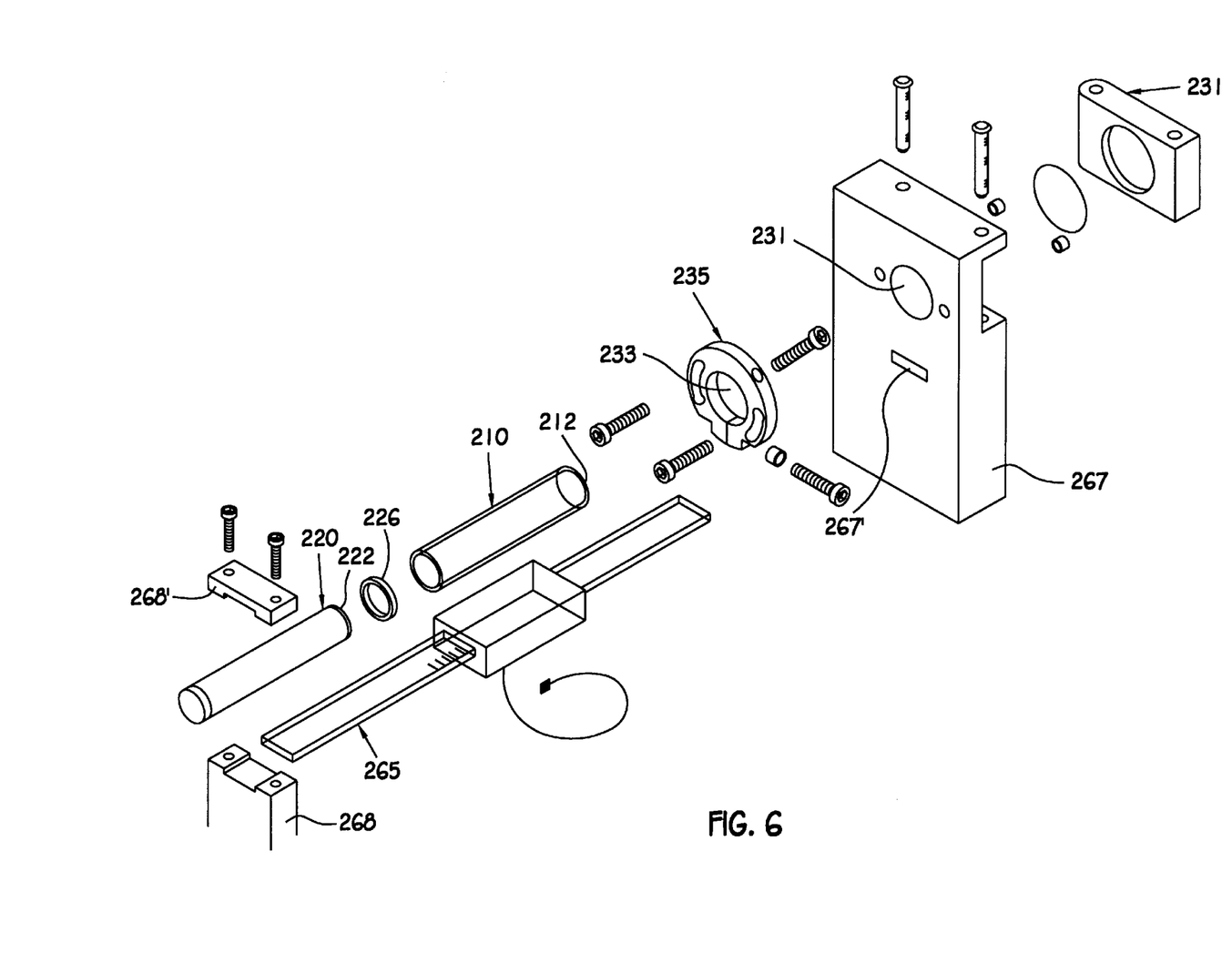
FIG. 6 shows an exploded perspective view of the various components of the entrapped gas measurement apparatus shown in FIG. 5.

In order to precisely measure pressure within the chamber of the assembly, it is important that the chamber be made air tight. In the FIG. 3 variation, vacuum chamber (140) is sealed by two opposite caps (142,144) each having gasket or O-ring seals, such as for example as is shown at O-ring (145) in FIG. 3. Likewise, as shown in FIG. 6, O-ring (226) provides a seal for barrel (210) and plunger (220) at end (222). Preferably the O-rings are made of soft rubber for a creating an efficient seal. In a pneumatic variation such as that shown in FIG. 3, vacuum chamber (140) is adapted for coupling to a negative pressure source, as is shown for example in FIG. 3 at threaded hole (146) which is adapted to attach chamber (140) to a mated fitting from a negative pressure source.

In general, the housing which defines the reservoir may be a variety of shapes, such as the barrel previously shown, a bulb reservoir, rectangular, ovular tube, etc. The reservoir may be any convenient receptacle for holding the sample as long as the reservoir is capable of changing its volume in a manner which may be detected accurately. In addition, the walls of the housing which form the reservoir, including a front wall, side walls and an end wall, may be made of any suitable material such as plastic, glass, and the like. Suitability of the material depends, inter alia, on the design of the syringe, sample type, and specific detector and processor embodiments chosen for detecting volumetric change of the sample and determining volume of entrapped air, respectively.

For example, for variations of the present invention which determine volumetric change of the reservoir and sample based upon the position of a moveable wall during expansion, the housing should be relatively rigid and non-expandable in all places but for the moveable wall being monitored. For the purpose of further illustration, where the rearward wall is made to move laterally within a barrel in a syringe embodiment as described above, the walls of the barrel are usually rigid and non-compliant. It is further preferred that at least a portion of the walls be a transparent material in order to view the sample, although the material may be opaque as well. In addition, the construction of the various components which comprise the reservoir chamber may also be of different materials.

In one specific example, the rearward wall is constructed of a metal such as stainless steel or aluminum. The front wall is constructed of an elastomeric disk such as of silicone with a rigid backing such as aluminum, which construction is believed to provide both the elastomeric feature for sealing the door to the housing as well as relative rigidity against biasing the elastic disk inward into the reservoir chamber under the applied vacuum. The barrel is constructed of glass.

However, for further illustration, the front wall and barrel may instead be constructed of hard polymer, such as for example polycarbonate. Further to this alternative illustrative construction, an assembly which provides a hard polymeric front wall engaged to an adjustable door to open the chamber for loading the sample may require the addition of a gasket or other elastomeric sealing means to provide the desired gas tight seal in the closed door condition during testing.

In addition, it is believed that a controlled interface between the moveable, rearward wall of the plunger and the inner surface of the barrel which forms the reservoir in syringe variations may be critical to accurate determinations of entrapped gas in a tested sample within the apparatus. In one respect, the plunger must slide within the barrel easily and with little friction (which if excessive may be a source of error in correlating expansion of the sample to the applied force). In another respect, however, there must be a gas tight seal at this same interface. Therefore, a sealing gasket, such as a soft, compliant O-ring, should be provided at or adjacent to the rearward wall of the plunger. Suitable material constructions and designs for such O-rings depends upon various factor including the type of rubber comprising the O-ring, the outer diameter at the surface upon which the O-ring sits, and the inner diameter of the barrel.

In addition, the inner surface may be treated or modified to enhance the movement of the rearward wall on the plunger by optimizing the friction caused by the rearward wall sliding along the sides of the reservoir. It is believed that surfaces which are either too smooth or too rough will cause increased friction that may be detrimental to functional results. Therefore, it may be desirable to create a texture on the reservoir internal surface to a desirable roughness, such as for example through the controlled use of abrasives. It is further believed that a surface having a surface roughness between about $8-40\mu$ inches RMS, and more preferably between about $8-15\mu$ inches, may be preferred for syringe barrels constructed of glass or metal and for use with O-rings constructed of an elastomer such as silicone rubber. A tensile force tester may be used to measure the frictional component along the length of the reservoir as the wall moves in response to force on the plunger.

Usually, the rearward wall should contact the sample such that no voids are present between the sample and wall. However, it may be desirable in some instances to include an intermediary material between the sample and rearward wall of the plunger in order to provide a barrier between the rearward wall and sample so that a variety of sample types can be tested. The inclusion of such an intermediary material may be especially useful when the material sample to be tested is an abrasive or gritty material such as concrete. When an intermediary material is used, however, it is desirable that there be no voids between the sample, intermediary material and rearward wall.

In another respect to the plunger/sample interface, the O-ring may be positioned along the plunger rearwardly of the rearward wall. The plunger outer diameter is dimensioned with some tolerance gap in relation to the inner diameter of the barrel, and this gap is generally bridged by the O-ring. Therefore, placing the O-ring rearwardly of the rearward wall as just described leaves the gap between the plunger and barrel forward of the O-ring, which gap may contribute an additional, although small volume to the overall reservoir volume. It is therefore further contemplated that this additional volume or "dead space" may be accounted for in the overall calculations for measuring the amount of entrapped gas in the sample, as described in relation to various equations above. According to one specific approach to account for this space, the dead space may be measured by running the machine without a sample, the results of such a "test run" yielding the amount of gas in the reservoir when at the zero or ostensibly "no volume" state.

One example of an intermediary material of the type just described may be a lubricant which may be added to the reservoir, such as according to the following method: opening the reservoir at the end opposite the end wall, applying an air-free lubricating gel over the end wall surface, calibrating the detector to the zero position, and then filling the reservoir with sample. The amount of lubricant can vary and is typically a few millimeters thick or less.

Further to the variations for the entrapped gas measurement assembly just described for the present invention, the sample expansion phenomena upon which the invention is based requires a force applicator to provide a force onto the moveable wall outwardly of a reservoir which is defined in part by that wall. The present invention contemplates various mechanisms as suitable force applicators for applying negative pressure to the reservoir, e.g. pneumatic source as in a vacuum, mechanical force as in a device for pulling or pushing the moveable wall down the length of the housing in a direction away from the sample (thereby creating a vacuum on the sample), or other sources known in the art.

Figure 4:
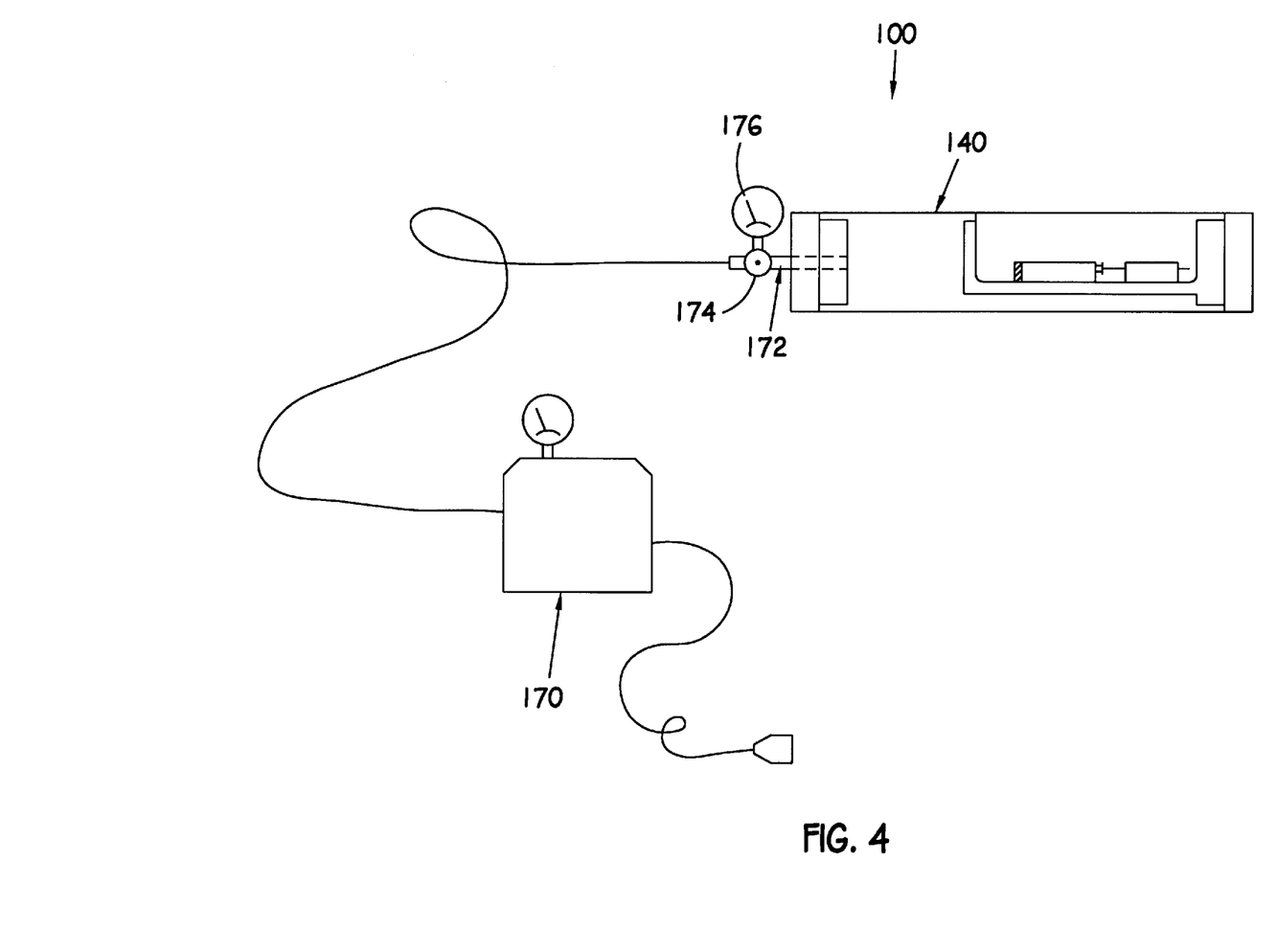
FIG. 4 shows a schematic diagram of the entrapped gas measurement apparatus shown in FIG. 3, and further shows a vacuum assembly which is coupled to the reservoir and material sample as a force applicator for providing a negative pressure on the material sample.

FIG. 4 shows a slightly different side view for entrapped gas measurement apparatus (100) shown in FIG. 3, and also provides a vacuum pump (170) as a force applicator which applies negative pressure to the sample to cause expansion of the sample. Vacuum pump (170) is pneumatically coupled to chamber (140) through attachment (172). A vacuum regulator (174) controls the amount of negative pressure applied to chamber (140) and vacuum gauge (176) reads the pressure within the chamber.

The amount of negative pressure applied depends, inter alia, on the type and amount of sample present and the volume of the reservoir. Typically the amount of negative pressure applied to the chamber is from about 5 inches to 30 inches Hg, more typically from about 10 inches to 27 inches Hg and preferably from 15 inches to 25 inches Hg. Preferably the vacuum pump is capable of producing 25 inches Hg when connected to a 110 V AC power source. The vacuum is preferably applied at a rate which is generally slow and consistent with the rate of sample expansion in order to avoid caving in of the sample or cavitation which may occur if vacuum is applied at a rate faster than sample expansion. The rate of change in applying the vacuum is generally from about 10 seconds to 300 seconds, more often from about 20 seconds to 120 seconds, and preferably from 30 seconds to 60 seconds, and usually about 30 seconds for most types of samples.

The present invention also contemplates various detectors as being suitable for use in monitoring and detecting the position of a moveable wall as a determinant of the expanding volume of a reservoir and material sample. One particular detector which is believed to be particularly beneficial for use in the present invention is shown in FIG. 5.

Figure 5:
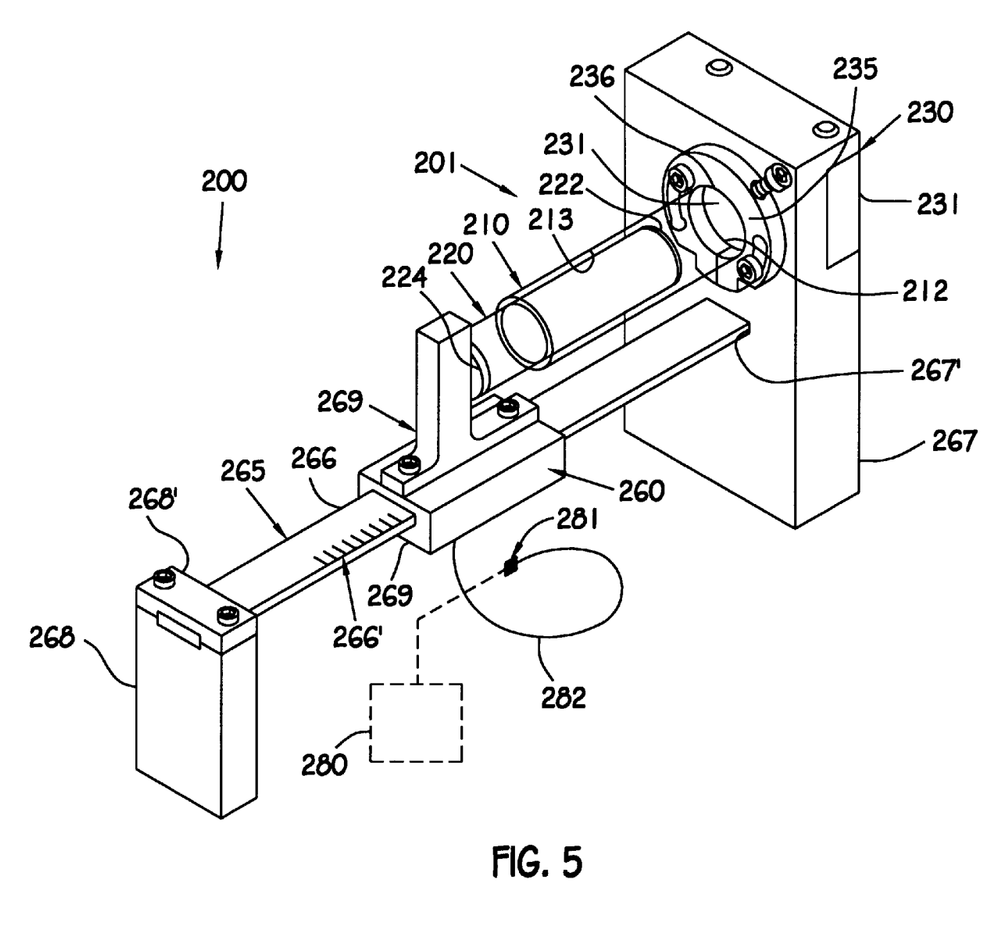
FIG. 5 shows a perspective view of another entrapped gas measurement apparatus according to the present invention.

FIG. 5 shows entrapped gas measurement assembly (200) to include a reservoir housing assembly (201) to include a barrel (210), plunger (220), and loading assembly (230) and is similar in structure and operation to the syringe-type reservoir housing assemblies shown previously in FIGS. 1A–B and FIGS. 3 and 4. However, the variation shown in FIG. 5 provides a rail (266) with which detection end (224) of plunger (220) is slideably engaged and along which a detector assembly (260) is adapted to detect the position and travel of the plunger.

In more detail to detector assembly (260) shown in FIG. 5, rail assembly (265) includes rail (266) which extends between a front support base (267) and a rearward support base (268). Detection end (224) of plunger (220) is secured to a rail coupler (269) which is slideably engaged with rail (266). Rail (266) has graduations (266') in predetermined, marked increments along its length. A linear measuring device marks the movement of rail coupler (269) along rail (266) according to graduations (266'), and is integral to the rail coupler (269) in the FIG. 5 variation and therefore not shown. Other position detectors than the specific "rail graduation monitoring" mode just described may also be suitable. In one example not shown, the detector may include an optical sensor optically coupled to indicia along the rail in order to indicate relative position of the plunger. In another example also not shown, the detector includes an electronic sensor coupled to the rail in a manner which indicates the relative position of the sensor and therefore the plunger. Further to this particular example, such electronic coupling may result in the desired indicia of relative sensor position via monitored electronic parameters of a circuit which couples the sensor to the rail, such as for example by a varied capacitance, inductance, or resistance monitored by the sensor as the plunger is moved.

The linear measuring device is coupled with processor (280) (shown in FIG. 5 schematically and in shadow) by use of a data cable (282) which transfers the detected position of the plunger to processor (280) via connector (281). Preferably, processor (280) includes a microprocessor or CPU which is adapted to receive detected signals through the connector such as through an RS232 coupling according to one of ordinary skill. The CPU according to such a variation would be further adapted to process the detected positioning signal according to the relationships described above between position, pressure, and entrapped gas volume, such as through software provided within the CPU or readable memory coupled to the CPU.

Figure 7:
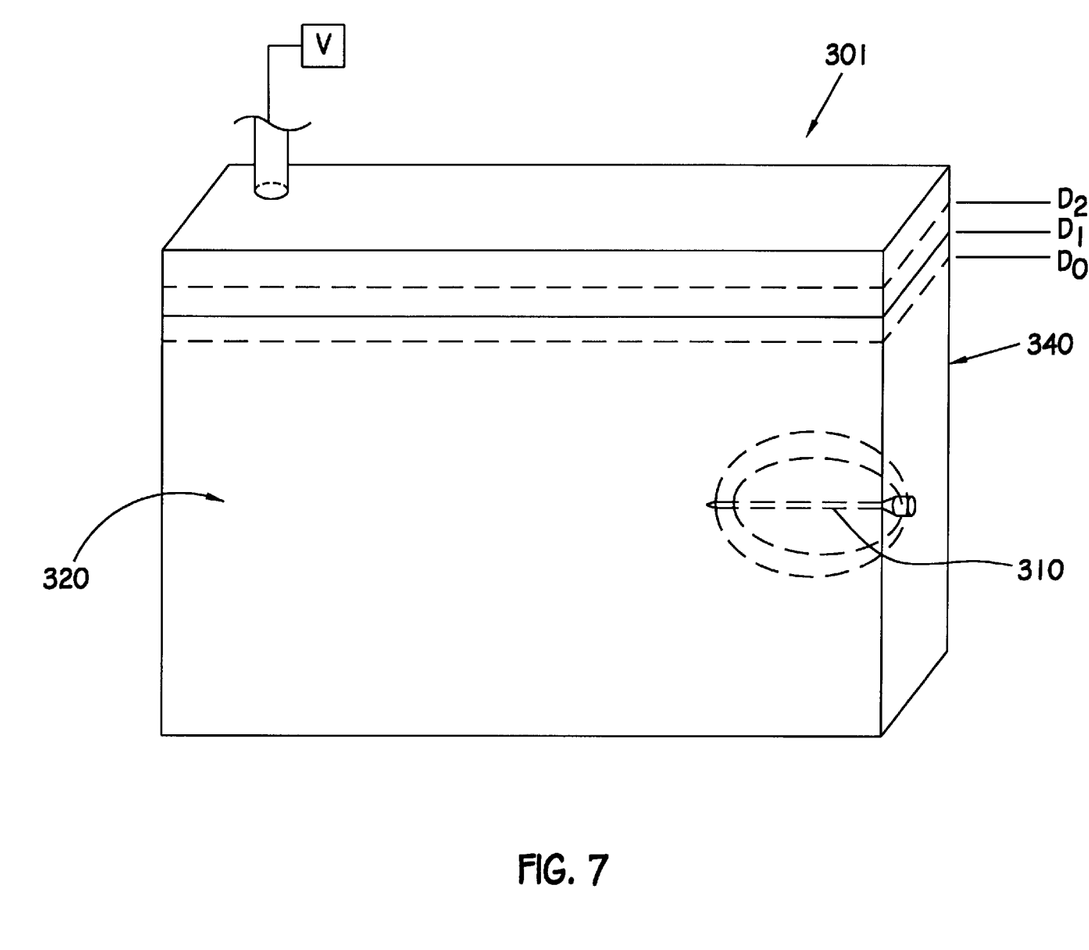
FIG. 7 shows a perspective view of another entrapped gas measurement apparatus according to the present invention.

More specific details of the components which make up entrapped gas measurement apparatus (200), including various attachment mechanisms, are shown in FIG. 7, and in more specific detail in exploded view in FIG. 6 and are described as follows.

Reservoir housing assembly (201) includes a barrel (210) with an inner surface (213) which defines an inner bore that extends between a front end (212) and a rearward end (214). The inner bore of barrel (210) in the region of its front end (212) is engaged to and registered with opening (233) of loading assembly (230). Loading assembly further includes a door (231) which is adapted to removably engage and interchangeably open or close opening (233) such that a sample (not shown), intermediary materials, etc., may be added to the barrel and then enclosed therein. Barrel (210) is adapted to secured to loading assembly (230) on front support base (267) by locking ring (235) and associated screws and inserts such that the aperture (236) in locking ring (235) aligns with the front end (212) of the barrel and loading assembly opening (233). The door (231) is sealed against base (267) with a gasket, and the loading assembly elements are further secured by additional pins. It is further contemplated that the sealing gasket for door (231) may be constructed of a specifically chosen material, which may be different to the material comprising the remaining mass of the door. This is due to the fact that this portion may be in direct contact with the sample during testing, and the particular material may depend upon the type of material sample used.

Front end (222) of plunger (220) which forms the rearward wall of the resulting reservoir is adapted to engage the inner bore of barrel (210) at the opposite extremity at which the barrel is secured to the loading assembly. Detection end (224) of plunger (220) extends externally of the barrel in order to engage rail coupler (269).

Further to the detailed components of rail assembly (265) as shown variously in FIGS. 5 and 6, one end of rail (266) is coupled to rearward support base (268) by base cap (268') with associated screws. The rail's other end is inserted into front support base (267) at aperture (267').

The previously described embodiments above generally share use of a relatively rigid reservoir but for a moveable wall which is monitored during sample expansion. However, as previously described a wide variety of sample reservoirs, force applicators, and detectors which may be used in combination and still fall within the scope of the present invention, so long as a negative pressure is applied to a material sample and the material sample's expansion under that vacuum is detected and used to determine the amount of entrapped gas within the sample. FIG. 7 shows a further entrapped gas measuring apparatus embodiment which exemplifies such a broad scope, wherein the entire reservoir is expandable under applied negative pressure.

More particularly, FIG. 7 shows a reservoir housing assembly (301) that includes an elastic container, which is shown in a particular variation in FIG. 7 to be a bulb (310). Bulb (310) is submersed in a non-compressible liquid (320) such as water. A fluid chamber (340) contains the liquid to a base level $D_0$, which indicates the bulb's volume being substantially zero prior to inserting a material sample within the bulb. Preferably, bulb (310) is submersed a sufficient depth under the liquid level such that a positive pressure actually forces the bulb to the substantially zero volume state. After the bulb is filled with a material sample, such as by injecting the sample within the bulb, an initial liquid level is measured as $D_1$, which is analogous to the first position of the plunger in the previous syringe-type embodiments. Negative pressure is then applied to the liquid from a pressure source (not shown) and imparted onto the sample. Expansion of the sample upon exposure to the pressure causes the bulb to expand thereupon changing the level of the fluid to $D_2$. The change in fluid level is measured as representative of sample expansion and the amount of gas entrapped in the sample.

The amount of entrapped gas may be calculated in large part by using the relationships between changing volume and pressures described by reference to the previous embodiments above or variations thereto. One variation which may better accommodate the present embodiment of FIG. 7 may include a pressure offset for an initial equilibrium pressure that is not atmospheric pressure, but is instead dependent upon the bulb's depth within the fluid bath. Alternatively, the zero volume point may be set after an initial application of an offset vacuum force which itself accommodates this pressure offset due to the bulb's depth.

In addition, according to the compliant reservoir variation of FIG. 7, the expansion of the bulb under pressure will be partially related to the mechanic stress-strain properties which are characteristic of the material used for the bulb. Therefore, the formulas used to extrapolate the amount of gas present in the sample may require compensation for this component of the bulb's expansion. Further to this aspect, it is preferable that the material and pressures are chosen for testing such that the bulb expands only along a substantially linear portion of the bulb material's characteristic stress-strain curve in order to best accommodate this offset to the expansion/entrapped air relationships.

Entrapped gas measurement assemblies according to the embodiments previously shown and described for the mechanical features of the invention preferably interface with automation instrumentation. The entrapped gas measurement assembly is used in conjunction with a conventional microprocessor, such as a computer to calculate the amount of gas present in the sample. Instrumentation can also be employed to record and store data, perform statistical analysis of replicate measurements, maintain temperature, control negative pressure in the chamber, correct for variations in barometric pressure relative to standard atmospheric pressure, etc. A printer can also be incorporated into the system to provide a hard copy of the results. With the assistance of the instrumentation, the gas measurement system is easy to operate, requiring little expertise by the user.

In use of the syringe-plunger configurations of the invention previously described above, the operator adds the sample to the reservoir. The reservoir and accompanying syringe-plunger components may be positioned in a horizontal position in the vacuum chamber, although it is believed that frictional sources of error are best minimized by placing the reservoir assembly vertically, especially where the sample may flow out of the reservoir. Where the device includes a removeably engageable front end wall, the end wall may be removed from the reservoir to add the sample and the end wall inserted into the reservoir to firmly contact the sample. Alternatively, the sample is added through a loading assembly at the front end of the reservoir to contact the end wall and the end wall remains in place, such as the door in the loading assemblies previously shown and described above. Moreover, the plunger and barrel of the syringe-type reservoir may be removed and loaded and then replaced back into the chamber. Which ever method is used to add the sample to the reservoir, the procedure should disallow excessive handling of the sample in order to avoid de-aeration of the sample.

The present invention is adapted for use with a variety of materials as material samples for testing, and in particular is amenable to materials constructed of substrates which allow for the expansion of the gas entrapped by the substrate when a sample of the material is exposed to an applied negative pressure. More specific examples of materials contemplated for use with the present invention include: finely divided solids, e.g. powders; semi-solids, e.g. gels; and liquids, e.g. ointments. The amount of sample also may vary depending on the type of sample used and reservoir size, typically from about 0.5 to 100 ml, more typically from about 1 to 10 ml and preferably from 2 to 5 ml. It is further believed that the invention may also be useful in determining the amount of entrapped gas within certain material samples of open cell solids, or elastic closed cell solids, e.g. closed cell foam elastomers.

Some such test materials as just described may include substrates which yield under applied vacuum and therefore contribute to the overall expansion of a material sample during evaluation according to the present invention. It is believed that the present invention may still be amenable to use with such materials, so long as the yield of the respective substrate is predictable, such as for example calculable for a measured weight of the sample. In such a circumstance, the calculations used to determine the amount of entrapped air based upon measured sample expansion, as provided above, may include still a further factor which accounts for such substrate expansion to thus remove what may otherwise be error in the overall entrapped gas determination. Moreover, material samples having a known viscosity in a particular reservoir chamber may also present some amount of fluid shear along the boundaries the chamber walls which may also contribute to the overall material expansion under applied vacuum in combination with the expansion of the entrapped air. It is also further contemplated that the predictability and amount of such shear forces may be calculable and accounted for in the operable calculations in order to accurately make the overall determination of the amount of entrapped gas in the sample according to the present invention.

It is further contemplated that, as the sample expands during testing with an apparatus according to the present invention, the temperature of the inside of the reservoir may decrease. However, with small sample sizes, any temperature fluctuation which occurs is generally negligible. With large sample sizes, however, the temperature may decrease to a greater extent and temperature may be monitored with a sensor and compensated for in calculating sample volume. For example, such compensation may be made by use of known relationships according to the gas law: PV=nRT where P is pressure, V is volume, n is moles, R is a constant and T is temperature.

After the volume of the sample has arrived at relative equilibrium and ceases to substantially expand further, the vacuum pressure is stabilized and the volume of the reservoir is detected. This equilibrium point may be identified visually with manual control to stabilize the pressure and take a measurement with the detector and processor, or more automated feedback control mechanisms may be employed. For example, the detector and/or processor may be preset to identify a predetermined value which represents equilibrium, such as a predetermined slope or time rate of change of the wall movement. Upon identifying that such a predetermined set-point is reached, the pressure may then be automatically adjusted and measurement taken from the detector for the purpose of determining the amount of entrapped gas. Regardless of the specific mechanism used for determining the equilibrium point, the amount of volumetric change is related to the amount of entrapped gas in the sample, conveniently by a computer or other automated means.

The present invention further contemplates particular methods for using the entrapped gas measuring apparatus embodiments previously described above by reference to the Figures, which methods of use are believed to be particularly beneficial in the production of materials with known amounts of entrapped gas.

One exemplary method for using the apparatus of the present invention in the production of a material with known entrapped gas volume is provided as follows. A first material is made according to a first method, such that a first amount of entrapped gas is present in the material. The amount of entrapped gas in this first material is then measured according to at least one of the assemblies and methods of use previously described above by reference to the embodiments in the Figures. The measured amount of entrapped gas in the material sample is then compared with detecting a predetermined range for entrapped gas volume or amount. If the measured amount is within the predetermined range, then the first sample is acceptable and is made with a predetermined amount of entrapped gas.

Thus a "predetermined amount of entrapped gas" is herein intended to mean an amount which is either a specific amount, such as actual volume or percent volume of the sample, or within a particular predetermined range. Further to this intended meaning, the "predetermined amount of entrapped gas" may be either substantially zero (it is believed that most all manufactured substances have some residual amounts of entrapped gas, although in many circumstances negligibly small), or may be a non-zero amount, such as according to methods intended to provide a desired amount of entrapped gas in a material or according to other methods intended to remove all gas in a material but allowing for some measurable tolerance which reflects a range of values bounded at zero.

If the determined amount of entrapped gas in the first material sample is not within the predetermined range, then a second material is made according to a second method, wherein the second method is intended to affect the resulting amount of entrapped gas in a desired direction from the first method and material (either increasing or decreasing the resultant amount as required). For example, the first method may employ a particular operating parameter which affects the amount of entrapped gas in the material produced, and the second method may be a modification of the first method wherein the operating parameter is adjusted based upon the determined entrapped gas amount in the first sample produced by the first method. The second material is then tested with the inventive apparatus and method and compared with the predetermined range. Such iterations may be repeated until a resulting material finally meets the required entrapped gas volume.

Further to this method of producing a material sample of known amount of entrapped gas, other parameters than actual expanded volume may be compared against predetermined ranges for such parameters. For example, the position of a moveable wall defining the reservoir, as previously described above, may be such a suitable parameter. In addition, the method just described is believed to be useful with a variety of specific methods for constructing various materials as would be apparent to one of ordinary skill.

EXAMPLE

For the purpose of further illustration, the following is an example of entrapped gas volume determinations for certain material samples, in particular commercially available whipping cream, using an entrapped gas measurement apparatus and method which exemplifies the various particular embodiments described above. For all of the examples provided below, a control method is used to determine the density of the material samples, such as for example by use of a specific gravity bottle or pycnometer, such as Model 1620-25 which is commercially available from Corning, Inc. A control measurement for the amount of entrapped air of a sample is made by measuring and comparing density before and after introduction of air into the sample. The amount of entrapped gas in the sample is also determined by use of an entrapped gas measurement assembly according to the present invention, and is compared against the control methods.

More specifically, a 15 ml syringe is used with a plunger at a position ($D_0$) designated as zero prior to sample addition. The plunger is removed and a sample consisting of 3 ml Clover Stornetta Heavy Whipping Cream (from Clover Stornetta Corporation, located Sonoma, Calif., Lot # 2045) is placed inside of the syringe. The whipped cream is pre-beaten in order to entrap gas in the standard method and until the whipped product is at its stiff peak stage. The plunger is replaced inside of the syringe to contact with the Cream. The position of the plunger (D1) is detected by a linear position detector and the pressure of the syringe (Pa) at atmospheric pressure is measured in inches Hg. The data are recorded by a computer. Next, an attached vacuum pump (Model SOAV105NA from GAST Manufacturing Corporation, located in Benton Harbor, Mich.) is activated to create a vacuum pressure inside of the syringe. After about 1 minute, the sample has expanded to substantial equilibrium and the vacuum is stabilized. The position of the plunger (D2) and the pressure inside of the syringe (P2) are again detected. The amount of change is related to the amount of entrapped gas in the sample. From this data, density of the sample is determined. The results of two tests according to the test method just described are as follows:

| Test 1 | |
|---|---|
| D (in) = | 0 |
| D1 (in) = | 0.6835 |
| D2 (in) = | 1.9642 |
| Pa in Hg = | 30 |
| P2 vac. in Hg = | 25 |
| % Entrapped Gas Result (Gas Volume * 100/Sample Volume): | |
| Vacuum/Expansion method = | 37.47 |
| Densitometer/Control method = | 36.87 |

| Test 2 | |
|---|---|
| D (in) = | 0 |
| D1 (in) = | 0.5975 |
| D2 (in) = | 1.313 |
| Pa in Hg = | 30 |
| P2 vac. in Hg = | 22 |
| % Entrapped Gas Result (Gas Volume * 100/Sample Volume): | |
| Vacuum/Expansion Method = | 43.55% |
| Densitometer/Control Method = | 42.44% |

The present invention has been described above in varied detail by reference to the particular embodiments and Figures. However, it is to be further understood that other modifications or substitutions may be made to the devices and methods described based upon this disclosure without departing from the broad scope of the invention.

What is claimed is:

1. An assembly for measuring an amount of entrapped gas in a material sample in a test environment, comprising:
   (a) a reservoir configured to receive the material sample, said reservoir having first and second sections, said second section being adjustable in position relative to the first section from a first position to a second position such that the reservoir has an adjustable volume from a first volume to a second volume, respectively, when the material sample is received within the reservoir and a predetermined pressure which is negative relative to atmospheric pressure in the test environment is applied to the reservoir, the position of the second section relative to the first section being indicative of the volume of the reservoir;
   (b) a detector coupled to said second section and configured to measure the position of the second section relative to the first section;
   (c) a processor which is coupled to the detector and which is configured to determine an amount of entrapped gas within the material sample received within the reservoir based upon a change in the position of the second section from the first position to the second position; and
   (d) a vacuum chamber enclosing said reservoir and configured to apply said negative pressure to said reservoir;
   (e) wherein said material sample expands in response to application of said negative pressure to said reservoir,
   (f) wherein the first volume of the reservoir is substantially equal to the volume of the material sample at atmospheric pressure in the test environment,
   (g) wherein the second volume of the reservoir is substantially equal to the volume of the material sample when the material sample expands after applying the negative pressure to the reservoir, and
   (h) wherein the differential between said second volume of said reservoir and said first volume of said reservoir is indicative of the amount of gas entrapped in said material sample.

2. The assembly of claim 1, wherein
   the reservoir is further defined by a reservoir chamber which is relatively rigid,
   the wall has a zero position relative to the reservoir chamber which is characterized by the reservoir's volume being substantially equal to zero prior to receiving the material sample within the reservoir, and
   the processor determines the amount of entrapped gas at atmospheric pressure in the test environment by the equation: $(d_2-d_1)/(d_1-d_0)*100$, such that $d_0$ is the zero position, $d_1$ is the first position, $d_2$ is the second position, $P_a$ is the atmospheric pressure in the test environment, and $P_v$ is the negative pressure applied to the reservoir.

3. The assembly of claim 2, wherein the housing further comprises:
   a syringe with a barrel and a plunger, the barrel having a front end and a rearward end and also an inner surface which forms an inner bore with a longitudinal axis that extends between the front and rearward ends, and the plunger having a front end and a rearward end; and
   a front wall which is engaged to and is adapted to form a gas tight seal with the front end of the barrel,
   wherein the front end of the plunger is engaged within the barrel's inner bore through the rearward end of the barrel and includes the wall as a rearward wall which is slideably coupled to the barrel's inner surface with a gas tight seal between the inner bore and the rearward end of the barrel,
   wherein the reservoir is defined by the front wall, the barrel's inner surface, and the rearward wall, and
   wherein the first and second positions of the wall are along the longitudinal axis of the inner bore.

4. The assembly of claim 1, wherein the processor is adapted to determine the amount of entrapped gas as a percent volume of the material sample which represents an actual volume of entrapped gas within the material sample divided by the volume of the material sample.

5. The assembly of claim 4, wherein the processor is adapted to determine the actual volume of entrapped gas within the material sample by multiplying the percent volume of entrapped gas by the volume of the material sample.

6. The assembly of claim 5, wherein the material sample further comprises a substrate, and the processor is adapted to determine a volume of the substrate by subtracting entrapped gas volume from the overall material sample volume.

7. The assembly of claim 6, wherein the processor is further adapted to determine a density of the substrate by dividing the substrate mass by the substrate volume.

8. The assembly of claim 1, wherein the sample is selected from the group consisting of semi-solids, finely divided solids, and liquids.

9. The assembly of claim 1, further comprising a vacuum source in fluid communication with said vacuum chamber, wherein said vacuum chamber sealably encapsulates said reservoir, and wherein said vacuum source applies a negative pressure within the vacuum chamber to effect a reduction in pressure surrounding said reservoir and a corresponding expansion of said reservoir as a result of expansion of the sample under reduced pressure.

10. A method for measuring an amount of entrapped gas within a material sample in a test environment, said material sample having a volume which is adjustable under an applied negative pressure, comprising the steps of:

(a) placing the material sample in an expandable reservoir;

(b) placing said reservoir in a vacuum chamber;

(c) applying negative pressure to the reservoir, said negative pressure being negative relative to atmospheric pressure in the test environment such that the reservoir expands from a first volume to a second volume as a result of expansion of said material sample;

(d) detecting the expansion in volume of said reservoir from the first volume to the second volume; and (e) determining an amount of entrapped gas in the sample based on the expansion from the first volume to the second volume wherein the differential between said second volume and said first volume is indicative of the amount of gas entrapped in said material sample.

11. The method of claim 10, further comprising the step of:

(f) determining the amount of entrapped gas in the material sample either as a percent volume of the entrapped gas within the material sample relative to an overall volume of the material sample or an actual volume of entrapped gas within the material sample.

12. The method of claim 11, wherein the reservoir is defined at least in part by a barrel and a plunger, the plunger having a plunging end which includes a wall and which is slideably engaged with the barrel, and further comprising the steps of:

detecting an initial position of the wall prior to applying the negative pressure to the reservoir;

detecting an adjusted position of the wall after initially applying the negative pressure to the reservoir; and determining the amount of entrapped gas within the material sample based upon the adjusted position of the wall relative to an initial position of the wall prior to applying the negative pressure to the reservoir, and further based upon the first volume.

13. The method of claim 12, further comprising the step of detecting a zero position of the wall prior to adding the material sample to the reservoir; and determining the first volume based upon the initial position relative to the zero position.

14. The method of claim 12, wherein the plunger further has a detection end which is separated from the plunging end with a shaft and which extends externally of the barrel when the plunging end is engaged within the barrel, and further comprising the step of:

detecting the position of the wall by detecting a position of the detection end of the plunger.

15. The method of claim 10, further comprising the steps of:

(f) adding the material sample to a reservoir having a reservoir volume and which is defined at least in part by a wall having an adjustable position relative to the reservoir, the reservoir volume being adjustable by adjusting the position of the wall and further being substantially equal to the material sample volume;

(g) isolating the material sample within the reservoir with a substantially gas tight seal;

(h) after isolating the material sample within the reservoir, applying said negative pressure to the wall outwardly of the reservoir such that the position of the wall is adjusted from a first position to a second position, which first and second positions characterize the first and second volumes, respectively; and (i) detecting the change from the first volume to the second volume by detecting at least one of the reservoir volume or the position of the wall.

16. The method of claim 10, further comprising the steps of:

coupling a vacuum source to the vacuum chamber; and applying said negative pressure to the reservoir with the vacuum source outwardly of the vacuum chamber.

* * * * *